US00PP35967P2

(12) United States Plant Patent
Kordes

(10) Patent No.: US PP35,967 P2
(45) Date of Patent: Jul. 9, 2024

(54) GRANDIFLORA ROSE PLANT NAMED 'KORinye'

(50) Latin Name: *Rosa hybrida*
Varietal Denomination: KORinye

(71) Applicant: W. KORDES' SÖHNE ROSENSCHULEN GMBH & CO KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/396,785

(22) Filed: Dec. 27, 2023

(51) Int. Cl.
*A01H 5/02* (2018.01)
*A01H 6/74* (2018.01)

(52) U.S. Cl.
USPC ..... Plt./132
CPC ..... *A01H 6/749* (2018.05)

(58) Field of Classification Search
USPC ..... Plt./132
CPC ..... A01H 5/0222
See application file for complete search history.

(56) References Cited

U.S. PATENT DOCUMENTS

PP20,711 P2 2/2010 Meilland

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of grandiflora rose plant, referred to by its cultivar name, 'KORinye', is described. The new variety forms in abundance on a substantially continuous basis attractive, red to burgundy and pink striped blossoms. The vegetation is vigorous, and the growth habit is very bushy. Attractive semi-glossy, dark green foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORinye'.

STATEMENT REGARDING PRIOR DISCLOSURES BY THE INVENTOR

The first offer for sale of the new variety was May 10, 2023. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of Grandiflora rose plant of the present invention was created by controlled breeding in 2013 in Sparrieshoop, Germany by artificial pollination wherein two parents were crossed which previously had been studied in the hope that they would contribute the desired characteristics. The female parent (i.e., the seed parent) of the new variety was the 'KORbimsala' variety (not patented). The male parent (i.e., the pollen parent) of the new variety was the 'KORblohawa' variety (not patented).

The parentage of the new variety can be summarized as follows:

'KORbimsala' x 'KORblohawa'

The seeds resulting from the above pollination were sown and small plants were obtained which were physically and biologically different from each other. Selective study resulted in the identification of a single plant of the new variety.

The new variety has been found to undergo asexual propagation at Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of grandiflora rose plant of the present invention possesses the following combination of characteristics:

(a) forms attractive, red to burgundy and pink striped blossoms,
(b) exhibits a very bushy growth habit, and
(c) provides semi-glossy, dark green foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the 'KORbimsala' variety (i.e., the seed parent) displays a less bushy growth habit and exhibits flowers with less petals compared to the new variety. Additionally, the new variety provides a striped flower color and larger sized flowers compared to the solid color flowers of the 'KORblohawa' variety (i.e., the pollen parent). Moreover, the new variety can be readily distinguished from non-parental related similar varieties. For example, the 'Meiroylear' variety (U.S. Plant Pat. No. 20,711) displays blossoms that are bright red with yellow stripes finishing to medium pink and cream, whereas the new variety displays red to burgundy and pink striped blossoms which have less petals compared to the 'Meiroylear' variety.

The new variety has been named the 'KORinye' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately four years of age and was grown outdoors in a field on its own roots in Cochranville, PA, USA in June 2023.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a four-year-old specimen of the new variety, observed during July, while growing on its own roots in a field in Cochranville, Pennsylvania.

Botanical classification: *Rosa hybrida* cultivar 'KORinye'.

Commercial classification: Grandiflora Rose.

Plant:

*Habit*.—Bushy.

*Height*.—Up to 92.0 cm from the top of the soil plane.

*Width*.—Up to 92.0 cm.

Branches:

*Stem color*.—Old wood is commonly Green Group 143A; young stems are commonly Green Group 143B.

*Length*.—Main stems: approximately 92.0 cm on average. — secondary stems: approximately 60.0 cm on average.

*Diameter*.—Main stems: approximately 1.0 cm on average. — secondary stems: approximately 5.0 mm on average.

*Thorns*.—Amount: moderate, 3 to 4 per internode. — young thorns: length is approximately 4.0 mm on average; width is approximately 3.0 mm at point of attachment; and color is commonly Greyed-Red Group 178A. — old thorns: length is approximately 7.0 mm on average; width is approximately 5.0 mm at point of attachment; and color is commonly Greyed-Orange Group 177A.

Leaflets:

*Number*.—5 and 7.

*Shape*.—Ovate; apex is acute to acuminate; and base is cuneate.

*Margin*.—Serrate.

*Undulation*.—Moderate.

*Glossiness of upper side*.—Semi-glossy.

*Texture*.—Upper surface: smooth. — under surface: smooth.

*Size*.—Terminal leaflet: length is approximately 5.5 cm on average; width is approximately 3.0 cm on average. — lower leaflets: length is approximately 3.5 to 4.0 cm on average; width is approximately 2.5 cm on average. — 5-Leaflet leaf: length is approximately 10.0 cm on average; width is approximately 8.5 cm on average.

Foliage:

*Young foliage*.—Upper surface color: commonly Green Group 138A. — under surface color: commonly Yellow-Green Group 144A with indistinguishable venation.

*Old foliage*.—Upper surface color: commonly Green Group 137A with indistinguishable venation. — under surface color: commonly Yellow-Green Group 146B with venation of Yellow-Green Group 145C.

*Petiole*.—Texture: upper surface is papillate; under surface is smooth. — length: approximately 1.5 cm on average. — width: approximately 1.0 mm on average. — upper surface color: commonly Yellow-Green Group 144A and Red Group 45A. — under surface color: commonly Yellow-Green Group 144A.

*Rachis*.—Length: approximately 2.0 cm on average. — width: approximately 1.0 mm on average. — upper surface color: commonly Green Group 143C. — under surface color: commonly Yellow-Green Group 144A.

*Stipules*.—Length: approximately 1.5 cm on average. — width: approximately 5.0 mm on average. — margin: entire to erose. — upper surface color: commonly Yellow-Green Group 146B. — lower surface color: commonly Yellow-Green Group 146B.

Inflorescence:

*Number of flowers*.—About 100 blooms on average on a plant at once.

*Number of blossoms per stem or in a cluster*.—Typically between 4 to 6 blooms per stem on average.

*Peduncle*.—Color: commonly Yellow-Green Group 144B. — diameter: approximately 5.0 mm on average. — length: approximately 5.0 cm on average. — surface texture: smooth.

*Sepals*.—Number: 5. — upper surface color and texture: commonly Yellow-Green Group 144A and Yellow-Green Group 144B, covered in short pubescence. — under surface color and texture: commonly Yellow-Green Group 144D, puberulent. — size: length is approximately 2.0 cm on average; width is approximately 1.0 cm on average. — margin: entire with extension on most sepals measuring 6.0 mm in length and 1.0 mm in width. — apex: acute to aristate. — base: truncate as it joins the receptacle.

*Buds*.—Shape: ovoid. — size: length is approximately 2.5 cm on average; width is approximately 1.5 cm on average. — color (when opening): striped/multi-colored commonly White Group N155C, Red-Purple Group 63A, and Red-Purple Group 60A.

*Flower*.—Form: double, cuplike. — profile: concave as it opens, and then outer petals are convex as the bloom ages and opens further. — diameter: approximately 6.0 cm on average. — height: approximately 3.0 cm on average. — duration: on the plant approximately 10 to 12 days. — petal color when first and fully opened: upper surface is striped/multi-colored commonly with Red Group 53A, Red Group 53B, Red Group 54A, Red-Purple Group 60A, Black Group 202A, Yellow Group 4C, and Yellow Group 2C with a basal spot commonly of Green-Yellow Group 1C to Yellow Group 2C; under surface is commonly Yellow Group 2D with a basal spot commonly of Green-Yellow Group 1C to Yellow Group 4C. — petal color at end of bloom: upper surface is striped/multi-colored commonly with Red-Purple Group 58A, Red-Purple Group 61A, Red-Purple Group 63A, and Red-Purple Group 61C with a distinct basal spot commonly of Green-Yellow Group 1C to Yellow Group 2C; under surface is commonly Yellow Group 2D with a basal spot commonly of Green-Yellow Group 1C to Yellow Group 4C.

*Fragrance*.—Slight sweet scent.

*Petal*.—Number: 40 on average. — drop: good. — length: typically 2.0 cm to 2.5 cm. — width: typically 1.7 cm to 2.2 cm. — overall shape: broadly obovate. — margin: entire with moderate undulation. — apex shape: rounded to slightly cuspidate. — base shape: cuneate.

*Petaloids*.—Number: 4. — length: approximately 2.0 cm on average. — width: approximately 8.0 mm on average. — color: multi-colored commonly including Red-Purple Group 59B, Red-Purple Group 62A and Green-Yellow Group 1D.

*Stamen*.—Number: approximately 105. — anthers: number is approximately 105; color is commonly Yellow-Orange Group 22A; length is approximately 2.0 mm on average; and shape is oval. — filaments: length is approximately 5.0 mm on average and color is commonly Yellow Group 12D.

*Pistils*.—Arrangement: separate and free. — number: approximately 45. — style: length is approximately 8.0 mm and color is commonly Green-Yellow Group 1A. — stigma: diameter is approximately 1.0 mm on average; shape is fan shaped.

*Receptacle*.—Diameter: approximately 8.0 mm on average. — depth: approximately 6.0 mm on average. — shape: urn shaped. — color: commonly Yellow-Green Group 144A. — surface texture: smooth.

*Pollen*.—Sparse, color is commonly Yellow-Orange Group 20A.

*Hips/seed*.—None observed.

Development:

*Vegetation*.—Semi-glossy, dark green, vigorous and strong.

*Blossoming*.—Abundant and continuous from spring through frost; typically, in bloom outdoors from May to November in Southeastern Pennsylvania.

*Resistance to diseases*.—Excellent resistance for black spot (*Diplocarpon rosae*), powdery mildew (*Sphaerotheca pannosa*), and rust (*Phragmidium* sp.).

*Hardiness*.—Hardy to USDA Zone 6, further hardiness testing is in process.

The new 'KORinye' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of grandiflora rose plant named 'KORinye' characterized by the following combination of characteristics:

(a) forms attractive, red to burgundy and pink striped blossoms, (b) exhibits a very bushy growth habit, and (c) provides semi-glossy, dark green foliage;

substantially as herein shown and described.

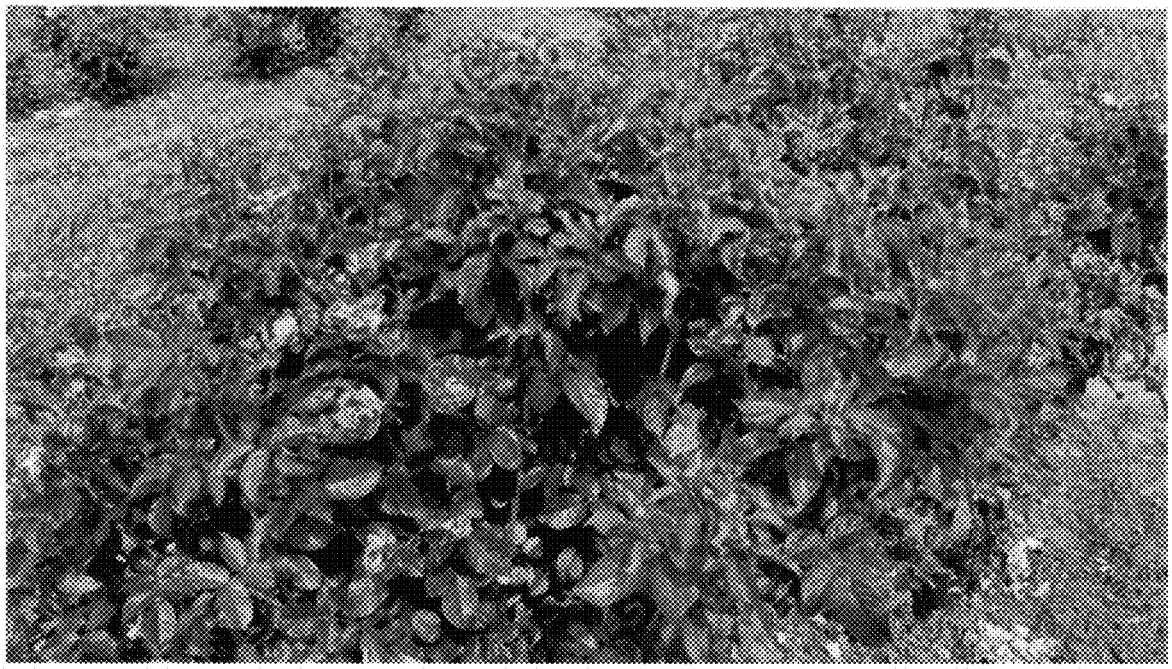

* * * * *